United States Patent
Bonnet et al.

(10) Patent No.: US 7,507,856 B2
(45) Date of Patent: Mar. 24, 2009

(54) METHOD OF OXIDISING HYDROCARBONS TO ACIDS

(75) Inventors: Didier Bonnet, Lyons (FR); Eric Fache, Caluire et Cuire (FR); Jean-Pierre Simonato, Sassenage (FR)

(73) Assignee: Rhodia Polyamide Intermediates, Saint-Fons (FR)

( * ) Notice: Subject to any disclaimer, the term of this patent is extended or adjusted under 35 U.S.C. 154(b) by 563 days.

(21) Appl. No.: 10/485,468

(22) PCT Filed: Jul. 15, 2002

(86) PCT No.: PCT/FR02/02508

§ 371 (c)(1),
(2), (4) Date: Jul. 8, 2004

(87) PCT Pub. No.: WO03/014055

PCT Pub. Date: Feb. 20, 2003

(65) Prior Publication Data

US 2004/0242922 A1    Dec. 2, 2004

(30) Foreign Application Priority Data

Aug. 3, 2001    (FR) .................................. 01 10427

(51) Int. Cl.
*C07C 51/16*    (2006.01)
*C07C 61/00*    (2006.01)
*C07C 51/31*    (2006.01)
(52) U.S. Cl. ........................ 562/412; 562/416; 562/509; 562/543
(58) Field of Classification Search .................. 562/543, 562/416, 412, 509
See application file for complete search history.

(56) References Cited

U.S. PATENT DOCUMENTS

| 2,223,493 | A | * | 12/1940 | Loder ......................... 562/543 |
| 3,649,685 | A | * | 3/1972 | Ishimoto et al. ............. 562/543 |
| 4,081,464 | A | | 3/1978 | Marsh et al. |
| 6,034,269 | A | | 3/2000 | Turner et al. |
| 7,041,848 | B2 | * | 5/2006 | Fache ......................... 562/543 |

FOREIGN PATENT DOCUMENTS

| EP | 0824962 | * | 2/1998 |
| FR | 2 806 079 A | | 9/2001 |
| GB | 845 038 A | | 8/1960 |
| WO | WO00/46172 | * | 8/2000 |

OTHER PUBLICATIONS

Solomons, Organic Chemistry, 1980, John Wiley & Sons, Inc., 2$^{nd}$ ed. p. 96-97 and 659-660. (p. 6).*
Aldrich catalog, 1998-1999, p. 296.*

* cited by examiner

*Primary Examiner*—Taylor Victor Oh
(74) *Attorney, Agent, or Firm*—Buchanan, Ingersoll & Rooney P.C.

(57) ABSTRACT

The present invention relates to a process for the oxidation of hydrocarbons, in particular of branched or unbranched saturated aliphatic hydrocarbons, of cycloaliphatic or alkylaromatic hydrocarbons or of alcohols and/or ketones, to acid or polyacid compounds.

It relates more particularly to the oxidation, by an oxidizing agent comprising molecular oxygen, of cyclohexane and/or of cyclohexanol and/or cyclohexanone to adipic acid, in the presence of an aromatic organic acid and a manganese-based catalyst. The yield and selectivity for adipic acid are of a high level with respect to those obtained with other solvents and catalysts.

25 Claims, No Drawings

METHOD OF OXIDISING HYDROCARBONS TO ACIDS

The present invention relates to a process for the oxidation of hydrocarbons, in particular of branched or unbranched saturated aliphatic hydrocarbons, of cycloaliphatic or alkylaromatic hydrocarbons and/or of alcohol/ketone compounds, to acid or polyacid compounds.

It relates more particularly to the oxidation, by an oxidizing agent comprising molecular oxygen, of cyclohexane and/or of cyclohexanol and/or cyclohexanone to adipic acid.

The oxidation of cyclohexane to adipic acid is a process which has been studied for many years. This is because adipic acid is an important chemical compound used as starting material in numerous manufacturing processes, such as the production of polymers, for example polyamides, polyesters or polyurethanes.

Several processes for the manufacture of adipic acid from hydrocarbons, such as benzene, phenol, cyclohexene or cyclohexane, have been provided.

The oxidation of cyclohexane, either directly or in two stages, is the most advantageous route for producing adipic acid.

Thus, U.S. Pat. No. 2,223,493, published in December 1940, discloses the oxidation of cyclic hydrocarbons to the corresponding diacids, in a liquid phase generally comprising acetic acid, at a temperature of at least 60° C., using a gas comprising oxygen, in the presence of an oxidation catalyst, such as a cobalt compound.

Many other patents and articles disclose this reaction for the direct oxidation of cyclohexane to adipic acid. However, to obtain acceptable yields for the production of adipic acid, these documents disclose the use of acetic acid as solvent in the presence either of a homogeneous catalyst or of a heterogeneous catalyst. Mention may be made, by way of illustration, of the article which appeared in the journal "Chemtech", 555-559 (September 1974), the author of which is K. Tanaka, which summarizes and comments on the process for the direct oxidation of cyclohexane. Mention may also be made of U.S. Pat. Nos. 3,231,608, 4,032,569, 4,158,73, 4,263,453 and 5,321,157 and European Patent 870 751, which disclose various homogeneous catalytic systems.

Processes for the direct oxidation of cyclohexane in the presence of a heterogeneous catalyst, such as aluminophosphates substituted by cobalt, have also been proposed, as in European Patent No. 519 569.

The choice of a solvent, namely acetic acid, is an important characteristic in obtaining an acceptable degree of conversion of the cyclohexane and an acceptable production of adipic acid. The use of such a solvent exhibits numerous disadvantages brought about by, for example, its corrosive nature under the temperature and pressure conditions used. Furthermore, the use of this solvent presents numerous problems in the stages for the separation and extraction of the adipic acid produced and the recycling of various compounds.

This is because, in the presence of acetic acid, it is difficult to separate and extract from the reaction mixture, the byproduct compounds from the oxidation, such as the cyclohexanone and the cyclohexanol formed.

In addition, the extraction of the adipic acid by crystallization and its purification are rendered difficult because the solubility under cold conditions of this acid is higher at 25° C. in acetic acid and lower at 80° C. in acetic acid than in water.

The separation and the recycling of the homogeneous catalyst are also difficult in the presence of acetic acid. In fact, on the one hand, recycling the catalyst without extracting the latter does not allow a sufficient catalytic activity to be retained and, on the other hand, the operations of separating the catalyst before recycling, as disclosed in particular in French Patents Nos. 2 722 783 and 2 746 671, are complex and expensive.

Furthermore, this solvent requires a difficult and expensive dehydration of the reaction mixture to be carried out.

Several processes for the oxidation of cyclohexane to adipic acid in a single stage without the use of acetic acid have also been provided. Some provide for carrying out this reaction in the absence of solvents and others with solvents, such as organic esters, for example acetates (U.S. Pat. No. 4,098, 817), acetone (U.S. Pat. No. 2,589,648) or alcohols, such as butanol, methanol, cyclohexanol or acetonitrile (EP 784 045).

These processes generally result in selectivities for adipic acid which are very low. Furthermore, the solvents used often exhibit low stability under the conditions for the oxidation of the hydrocarbon, such as cyclohexane. This low stability leads to a high consumption of the solvent, which renders such processes unusable.

One of the aims of the present invention is to provide a process for the oxidation of hydrocarbons in a single stage to produce acids or polyacids in a medium which is liquid under the conditions of the oxidation reaction which makes possible separation of the acid produced and recycling of the catalyst by simple operations with acceptable yields.

To this end, the invention provides a process for the oxidation of substituted or unsubstituted saturated aliphatic or cycloaliphatic hydrocarbons or of alkylaromatic hydrocarbons to acids or polyacids in a liquid medium by an oxidizing agent comprising molecular oxygen, characterized in that one of the constituents of the liquid medium is an organic acid compound of the following general formula (I):

in which:

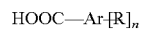

HOOC—Ar-[R]$_n$

Ar represents an aromatic radical containing an aromatic ring or several aromatic rings in condensed form, n represents an integer which may be equal to 1, 2 or 3, R represents a radical of the following general formula (II):

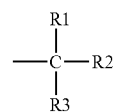

in which:

R1, R2 and R3, which are identical or different, represent an alkyl chain containing from 1 to 4 carbon atoms or a fluorine, chlorine or bromine atom.

According to the invention, the oxidation reaction is carried out in the presence of a manganese-based catalyst.

According to the invention, the compound of general formula (I) is advantageously chosen from the list of benzoic and naphthalenic acids which are advantageously substituted by tert-alkyl groups such as tert-butyl or by trifluorocarbon-based radicals. Mention may be made, as acids suitable for the invention, of 3,5-di-tert-butylbenzoic acid, 3,5-di-trifluoromethylbenzoic acid, 4-trifluoromethylbenzoic acid, 4-tert-butylbenzoic acid.

These acid compounds may be at least partially miscible with the hydrocarbon(s) to be oxidized, under the temperature and pressure conditions used for carrying out the oxidation reaction, and advantageously may be sparingly soluble in water, that is to say a solubility of less than 10% by weight at room temperature (10° C.-30° C.).

The term "at least partially miscible" should be understood as meaning that, under the conditions of the oxidation reaction, the solubility of one compound in the other is at least greater than 2% by weight and that a homogeneous liquid phase comprising at least a portion of the hydrocarbons to be oxidized and of the acid compound is formed.

In a preferred embodiment of the invention, the miscibility between the hydrocarbon and the above acid compound is such that, under the conditions of implementation of the invention, these two compounds form a single homogeneous liquid phase.

However, it is possible, without departing from the scope of the invention, to use organic compounds having a solubility in water greater than that indicated above if the coefficient of partition of this compound between the organic phase(s) of the reaction medium which essentially consist of the hydrocarbon to be oxidized, the oxidation intermediates and the nonorganic phase comprising the water formed during the oxidation reaction makes it possible to obtain a concentration of the organic compound of general formula (I) in the said aqueous phase of less than 10% by weight.

According to another characteristic of the invention, the concentration of acid compound in the reaction medium is determined in order to obtain a molar ratio between the number of mol of acid and the number of mol of manganese metal forming the catalyst of between 0.5 and 100 000, preferably between 1 and 5 000.

The concentration of acid compound in the liquid oxidation medium can vary within wide limits. Thus, it can be between 1 and 99% by weight with respect to the total weight of the liquid medium and it can more advantageously be between 2 and 50% by weight of the liquid medium.

It is also possible, without, however, departing from the scope of the invention, to use the acid compound in combination with another compound which can in particular have the effect of improving the selectivity and/or the productivity of the reaction for oxidation to adipic acid, and in particular the solubilization of oxygen.

Mention may in particular be made, as examples of such compounds, of nitriles, hydroxyimide compounds, halogenated compounds, more advantageously fluorinated compounds. Mention may be made, as more particularly suitable compounds, of nitriles such as acetonitrile, benzonitrile, imides belonging to the family described in patent application EP 0824962, and more particularly N-hydroxysuccinimide (NHS) or N-hydroxyphthalimide (NHPI), halogenated derivatives such as dichloromethane, fluorinated compounds such as:

cyclic or acyclic fluorinated or perfluorinated aliphatic hydrocarbons or fluorinated aromatic hydrocarbons, such as perfluorotoluene, perfluoromethylcyclohexane, perfluorohexane, perfluoroheptane, perfluorooctane, perfluorononane, perfluorodecalin, perfluoromethyldecalin, α,α,α-trifluorotoluene or 1,3-bis(trifluoromethyl)benzene perfluorinated or fluorinated esters, such as perfluoro(alkyl octanoate)s or perfluoro(alkyl nonanoate)s fluorinated or perfluorinated ketones or ethers, such as perfluoroacetone fluorinated or perfluorinated alcohols, such as perfluorohexanol, perfluorooctanol, perfluorononanol, perfluorodecanol, perfluoro-t-butanol, perfluoroisopropanol or 1,1,1,3,3,3-hexafluoro-2-propanol fluorinated or perfluorinated nitrites, such as perfluoroacetonitrile fluorinated or perfluorinated acids, such as trifluoromethylbenzoic acids, pentafluorobenzoic acid, perfluorohexanoic acid, perfluoroheptanoic acid, perfluorooctanoic acid, perfluorononanoic acid or perfluoroadipic acid fluorinated or perfluorinated halides, such as perfluoroiodooctane or perfluorobromooctane fluorinated or perfluorinated amines, such as perfluorotripropylamine, perfluorotributylamine or perfluorotripentylamine.

The oxidation is carried out in the presence of a catalyst. This catalyst comprises manganese as catalytically active metal element.

This catalyst is employed either in the form of compounds, advantageously at least partially soluble in the liquid oxidation medium under the conditions of implementation of the oxidation reaction (homogeneous catalyst), or supported on, absorbed on or bonded to an inert support, such as silica or alumina, for example (heterogeneous catalyst).

The catalyst is preferably, in particular under the conditions of implementation of the oxidation reaction:

either soluble in the hydrocarbon to be oxidized, or soluble in the acid compound, or soluble in the hydrocarbon/acid compound mixture forming a homogeneous liquid phase under the conditions of implementation of the reaction.

According to a preferred embodiment of the invention, the catalyst used is soluble in one of these media at room temperature or at the temperature for recycling these media in a new oxidation.

The term "soluble" is understood to mean that the catalyst is at least partially soluble in the medium under consideration.

In the case of heterogeneous catalysis, the catalytically active metal elements are supported or incorporated in a micro- or mesoporous inorganic matrix or in a polymeric matrix or are in the form of organometallic complexes grafted to an organic or inorganic support. The term "incorporated" is understood to mean that the metal is an element of the support or that the operation is carried out with complexes which are sterically trapped in porous structures under the conditions of the oxidation.

In a preferred embodiment of the invention, the homogeneous or heterogeneous catalyst is composed of salts or of complexes of manganese. The concentration by weight of metal, expressed as weight of manganese, in the liquid oxidation medium is advantageously greater than 10 ppm, preferably between 50 ppm and 25 000 ppm, and more advantageously still between 50 ppm and 5 000 ppm.

The invention applies more particularly to the oxidation of cycloaliphatic compounds, such as cyclohexane or cyclododecane, to the corresponding linear diacids, adipic acid and dodecanoic acid.

According to a preferred embodiment of the invention, it relates to the direct oxidation of cyclohexane to adipic acid by a gas comprising oxygen, in a liquid medium and in the presence of a manganese catalyst.

The oxidation reaction is carried out at a temperature of between 50° C. and 200° C., preferably between 70° C. and 180° C. It can be carried out at atmospheric pressure. However, it is generally carried out under pressure in order to keep the components of the reaction medium in the liquid form. The pressure can be between 10 kPa (0.1 bar) and 20 000 kPa (200 bar), preferably between 100 kPa (1 bar) and 10 000 kPa (100 bar).

The oxygen used can be in a pure form or as a mixture with an inert gas, such as nitrogen or helium. Use may also be made of air more or less enriched in oxygen. The amount of oxygen fed into the medium is advantageously between 1 and 1 000 mol per mole of compounds to be oxidized.

The oxidation process can be carried out continuously or batchwise. The liquid reaction medium which has exited from the reactor is advantageously treated according to known processes which make it possible, on the one hand, to separate and to recover the diacid produced and, on the other hand, to recycle the nonoxidized or partially oxidized organic compounds, such as cyclohexane, cyclohexanol and/or cyclohexanone, the catalyst and the acid compound.

The catalyst, in addition to manganese, can also comprise other compounds based on metals chosen from the group consisting of cobalt, copper, cerium, bromine, vanadium, chromium, zirconium, hafnium and a combination of some of these elements. It is in particular advantageous to combine the manganese with an element such as cobalt.

It is advantageous also to employ a compound which initiates the oxidation reaction, such as, for example, a ketone, an aldehyde or a hydroperoxide. Cyclohexanone and cyclohexyl hydroperoxide, which are reaction intermediates in the case of the oxidation of cyclohexane, are very particularly indicated. The initiator generally represents from 0.01% to 20% by weight of the weight of the reaction mixture employed, without these proportions having a critical value. The initiator is of use in particular during the starting of the oxidation. It can be introduced from the beginning of the reaction.

The oxidation can also be carried out in the presence of water, introduced from the initial stage of the process.

As indicated above, the reaction mixture resulting from the oxidation is subjected to various operations for the separation of some of its constituents in order, for example, to allow their recycling, to the oxidation and the recovery of the acids produced.

According to a first alternative form of the process, the crude reaction mixture can be first of all subjected to cooling, for example to a temperature of 16° C. to 30° C., which brings about the crystallization of at least a portion of the acid formed. A medium is thus obtained which comprises a solid phase composed essentially of acid, at least one liquid organic phase comprising essentially the unreacted compound to be oxidized, optionally the dissolved acid compound and the oxidation intermediates (or several organic phases, if the acid compound and the hydrocarbon are not completely miscible at low temperature) and a liquid aqueous phase comprising essentially acid byproducts from the oxidation and the water formed. The catalyst can be in one of the organic phases, if it is soluble in the said phase, or in the lower aqueous phase.

After filtering or centrifuging of the solid, the separation by settling of the organic and aqueous liquid phases constituting the filtrate or the centrifugate is carried out, if necessary; the organic phase or phases can be recycled in a further oxidation reaction.

It may be advantageous, prior to the operation of crystallizing the acid, to concentrate the reaction mixture.

According to a second alternative form of the process, the final crude reaction mixture can be withdrawn under hot conditions, for example at a temperature which can reach 75° C. The reaction mixture then separates by settling into at least two liquid phases: one or more organic phases comprising essentially the unreacted hydrocarbon, the acid compound and oxidation intermediates and a liquid aqueous phase comprising essentially the acids formed and the water formed. According to the solubility and the nature of the catalyst, the latter can be present in the organic phase or phases and can be recovered by solid/liquid separation before precipitation or crystallization of the acid formed, in the case of a heterogeneous catalyst, or extracted by liquid/liquid extraction, over resins or electrodialysis if it is soluble in the aqueous phase.

As in the first alternative form, the liquid phases are separated by settling; the organic phase or phases can be recycled in a further oxidation reaction.

In these embodiments, the acid compound used in accordance with the invention is generally present in or forms an essential component of the organic phase or phases. Consequently, after separation of the acid formed and optionally of the liquid phase comprising the water formed, the oxidation by-products, the catalyst and the acid compound are recycled in the oxidation stage with the nonoxidized hydrocarbon and the oxidation intermediates.

Furthermore, if the acid compound is solid in a phase of treatment of the reaction medium, it will advantageously be separated and recovered by employing solid/liquid separation processes, either before treatment of the reaction medium to recover the acid produced or with the acid produced. In the latter case, the acid produced can be recovered by extraction with water.

It is remarkable that the recovery of the acid compound should be almost total, that is to say that a very small quantity, which is practically nonmeasurable, of acid compound is converted during the reaction or carried with the adipic acid separated. Thus, the rate of recovery of the acid compound is greater than 97%.

In these exemplary embodiments of the invention, water can be added to the reaction medium to obtain better dissolution of the acid byproducts from the oxidation and better recovery of the acid formed.

The acid is generally recovered by precipitation during the cooling of the reaction medium. The acid thus recovered can be purified according to familiar techniques disclosed in numerous patents. Mention may be made, by way of examples, of French Patents Nos. 2 749 299 and 2 749 300.

If the nonorganic or aqueous liquid phase comprises the catalyst, the latter is extracted either before crystallization of the acid formed, by precipitation or extraction according to known processes, such as liquid-liquid extraction, electrodialysis or treatment over ion-exchange resins, for example, or after crystallization of the acid formed, by extraction techniques described above or similar techniques.

Other advantages and details of the invention will become more clearly apparent in the light of the examples given below purely by way of indication and illustration.

EXAMPLE 1

The following materials:
0.0344 g of Mn(acac)$_3$ (107 ppm expressed as Mn) (Acac: acetyl acetonate)
0.5594 g (5.71 mmol) of cyclohexanone
45.0965 (536.9 mmol) of cyclohexane
5.0157 g (28.17 mmol) of 4-tert-butylbenzoic acid are charged to a 125 ml titanium autoclave equipped with means for heating by a ring heater, with a turbine and with means for introducing gas and for regulating the pressure.

After closing the reactor, stirring at 1 000 revolutions per minute is applied, 125 bar of air (at 20° C.) are introduced and the heating is initiated. The bulk temperature reaches 140° C. in 10 minutes and is maintained for 25 minutes.

After cooling and depressurizing, the reactor is opened. The reaction mixture comprises a phase comprising cyclohexane and a precipitate. The whole is dissolved in acetic acid and the organic products are assayed by gas chromatography with the use of an internal standard.

The degree of conversion of the cyclohexane (DC) is 7.17%.

The results of the analyses are assembled in Table I below.

TABLE I

| Products | ST % |
|---|---|
| Adipic acid | 53.6 |
| Glutaric acid | 11.8 |
| Succinic acid | 3.5 |

The tert-butylbenzoic acid is quantitatively assayed at the end of the test.
ST %=selectivity for the compound indicated in the first column with respect to the cyclohexane converted.
DC %=degree of conversion of the cyclohexane EXAMPLES 2 to 6

The following materials:
0.0033 g of Mn(acac)$_3$ (106 ppm expressed as Mn) (Acac: acetyl acetonate)
0.0585 g (0.597 mmol) of cyclohexanone
5.00 (58.9 mmol) of cyclohexane
2 mol % of acid compound with respect to cyclohexane are charged to a 30 ml C22 alloy autoclave equipped with heating means and stirred by shaking.

After closing the reactor and placing under stirring, 100 bar of air (at 20° C.) are introduced and the heating is started. The reactor is thus stirred for 3 hours at 120° C. After cooling and depressurizing, the reactor is opened. The reaction mixture comprises a phase comprising cyclohexane and a precipitate. The whole is dissolved in acetic acid and the organic products are assayed by gas chromatography with the use of an internal standard.

The degree of conversion of the cyclohexane (DC), based on the assay of the products at the end of the test, is presented in Table II, for each acid compound used.

TABLE II

| Ex | Acid compound | DC cyclohexane % |
|---|---|---|
| 2 | without | 0.48 |
| 3 | 4-trifluoromethyl-benzoic acid | 2.32 |
| 4 | 4-tert-butylbenzoic acid | 3.64 |
| 5 | naphthanoic acid | 0.94 |
| 6 | benzoic acid | 1.65 |

EXAMPLES 7 to 10

The following materials:
x g of Mn(acac)$_3$ to obtain a catalyst concentration expressed in ppm of Mn indicated in Table III below
0.0525 g of cyclohexanone
4.5 g of cyclohexane
0.500 g of 4-tert-butylbenzoic acid are charged to a 30 ml C22 alloy autoclave equipped with heating means and stirred by shaking.

After closing the reactor and placing under stirring, 100 bar of air (at 20° C.) are introduced and the heating is started. The reactor is thus stirred for 3 hours at 120° C. After cooling and depressurizing, the reactor is opened. The reaction mixture comprises a phase comprising cyclohexane and the precipitate. The whole is dissolved in acetic acid and the organic products are assayed by gas chromatography with the use of an internal standard.

The DC of cyclohexane and ST for adipic acid are presented in Table III for various catalyst concentrations.

TABLE III

| | Ex | | | |
|---|---|---|---|---|
| | 7 | 8 | 9 | 10 |
| Mn (ppm) | 10 | 100 | 1 000 | 10 000 |
| ST AdOH % | 29.7 | 39.7 | 38 | 26.0 |
| DC cyclo % | 3.86 | 4.27 | 3.03 | 1.79 | ppm: parts per million by mass of manganese metal in the reaction medium

EXAMPLE 11

The following materials:
0.0154 g of Mn(acac)$_3$ (Acac: acetyl acetonate
0.0066 g of Co(acac)$_3$
0.5089 g of cyclohexanone
45.085 g of cyclohexane
5.002 g of 4-tert-butylbenzoic acid are charged to a 180 ml titanium autoclave provided with heating means.

After closing the reactor, stirring at 1 000 revolutions per minute is applied, 106 bar of air (at 20° C.) are introduced and the heating is initiated. The bulk temperature reaches 130° C. in 10 minutes and is maintained for 30 minutes.

After cooling and depressurizing, the reactor is opened. The reaction mixture comprises a phase comprising cyclohexane and a precipitate. The whole is dissolved in acetic acid and the organic products are assayed by gas chromatography with the use of an internal standard.

The degree of conversion of cyclohexane (DC) is 7.8%.

The quantity of products assayed at the end of the test is indicated below
adipic acid: 2.61 g
glutaric acid: 0.48 g
succinic acid: 0.13 g
cyclohexanol: 1.37 g
cyclohexanone: 0.61 g

EXAMPLE 12

Test 11 is repeated with the following load:
0.0158 g of Mn(acac)$_3$ (Acac: acetyl acetonate)
0.0060 g of Co(acac)$_3$
0.5164 g of cyclohexanone
45.109 g of cyclohexane
5.07 g of 4-tert-butylbenzoic acid After closing the reactor, stirring at 1 000 revolutions per minute is applied, 75 bar of air (at 20° C.) are introduced and the heating is initiated. The pressure of the reactor is maintained at 100 bar with a partial pressure of oxygen of 20 bar maintained with the aid of a pure oxygen reserve. The bulk temperature is maintained at 130° C. for 40 minutes. After cooling and depressurizing, the reactor is opened. The reaction mixture comprises a phase comprising cyclohexane and a precipitate. The whole is dissolved in acetic acid and the organic products are assayed by gas chromatography with the use of an internal standard.

The degree of conversion of cyclohexane (DC) is 10.1%.

The quantity of products assayed at the end of the test is indicated below
adipic acid: 3.94 g
glutaric acid: 0.71 g
succinic acid: 0.201 g
cyclohexanol: 1.4 g
cyclohexanone: 0.51 g

EXAMPLE 13

Test 11 is repeated with the following load:
0.0144 g of MnBr$_2$.4H$_2$O
0.0095 g of Co(acac)$_3$
0.5050 g of cyclohexanone
45.018 g of cyclohexane
5.037 g of 4-tert-butylbenzoic acid After closing the reactor, stirring at 1 000 revolutions per minute is applied, 75 bar of air (at 20° C.) are introduced and the heating is initiated. The pressure of the reactor is maintained at 100 bar with a partial pressure of oxygen of 20 bar maintained with the aid of a pure oxygen reserve. The bulk temperature is maintained at 130° C. for 30 minutes. After cooling and depressurizing, the reactor is opened. The reaction mixture comprises a phase comprising cyclohexane and a precipitate. The whole is dissolved in acetic acid and the organic products are assayed by gas chromatography with the use of an internal standard.

The degree of conversion of cyclohexane (DC) is 7.8%.

The quantity of products assayed at the end of the test is indicated below
adipic acid: 2.71 g
glutaric acid: 0.48 g
succinic acid: 0.13 g
cyclohexanol: 1.38 g
cyclohexanone: 0.74 g

The invention claimed is:

1. A process for the oxidation of substituted or unsubstituted cycloaliphatic hydrocarbons, cycloaliphatic alcohols and cycloaliphatic ketones to acids or polyacids said process comprising:
   (a) forming a medium comprising (i) at least one cyclic compound to be oxidized selected from the group consisting of cycloaliphatic hydrocarbons, cycloaliphatic alcohols and cycloaliphatic ketones and a mixture thereof, wherein said cycloaliphatic hydrocarbons, cycloaliphatic alcohols and cycloaliphatic ketones having a cycloaliphatic ring of from 3 to 12 carbon atoms, (ii) an oxidizing agent comprising molecular oxygen, (iii) a manganese-based catalyst and (iv) an organic acid compound of the following formula (I):

HOOC—Ar—[R]$_n$   (I)

in which:
   Ar represents an aromatic radical having an aromatic ring or several aromatic rings in condensed form,
   n represents an integer which may be equal to 1, 2 or 3, and
   R represents a radical of the following formula (II):

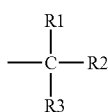

in which:
   R1, R2 and R3, which are identical or different, represent an alkyl chain having from 1 to 4 carbon atoms or a fluorine, chlorine or bromine atom; and
   (b) oxidizing said cyclic compound in a liquid medium at a temperature of between 50° C. and 200° C. and a pressure of between atmospheric and 200 bar to form an acid or polyacids.

2. The process according to claim 1, wherein the cyclic compound to be oxidized is at least partially miscible with the acid compound under the conditions of implementation of the oxidation reaction.

3. The process according to claim 1, wherein the aromatic radical, Ar, in formula (I) of the organic acid compound is selected from the group consisting of benzoic and naphthalenic radicals.

4. The process according to claim 3, wherein the benzoic and naphthalenic radicals are substituted by tert-alkyl or fluorocarbon-based groups.

5. The process according to claim 3, wherein the acid compound is selected from the group consisting of 3,5-ditert-butylbenzoic acid, 3,5-ditrifluoromethylbenzoic acid, 4-trifluoromethyl-benzoic acid and 4-tert-butylbenzoic acid.

6. The process according to claim 1, wherein the percentage by weight of acid compound in the liquid medium is between 1 and 99% by weight relative to the total weight of the liquid medium.

7. The process according to claim 6, wherein the percentage by weight of the acid compound is between 2 and 50% by weight.

8. The process according to claim 1, wherein the catalyst is soluble in the liquid medium under the conditions of implementation of the oxidation reaction.

9. The process according to claim 1, wherein the catalyst is insoluble in the liquid medium under the conditions of implementation of the oxidation reaction.

10. The process according to claim 9, wherein the catalyst is a supported catalyst comprising an inorganic or polymeric support.

11. The process according to claim 1, wherein the oxidation is carried out in the presence of a compound selected from the group consisting of nitriles, hydroxyimide compounds and halogenated compounds.

12. The process according to claim 11, wherein the compound is a nitrile compound selected from the group consisting of acetonitrile and benzonitrile.

13. The process according to claim 11, wherein the compound is a hydroxyimide compound selected from the group consisting of N-hydroxysuccinimide and N-hydroxyphthalimide.

14. The process according to claim 11, wherein the compound is a halogenated compound selected from the group consisting of cyclic or acyclic fluorinated or perfluorinated aliphatic hydrocarbons or fluorinated aromatic hydrocarbons, perfluorinated or fluorinated esters, fluorinated or perfluorinated ketones, fluorinated or perfluorinated alcohols, fluorinated or perfluorinated nitriles, fluorinated or perfluorinated acids, fluorinated or perfluorinated halides, and fluorinated or perfluorinated amines.

15. The process according to claim 1, wherein the cyclic compound to be oxidized is selected from the group comprising cyclohexane and cyclododecane.

16. The process according to claim 15, wherein the acid produced is adipic acid or dodecanedioic acid.

17. The process according to claim 1, wherein the liquid medium, after oxidation, is separated by settling into at least one organic phase formed by the nonoxidized hydrocarbon and the acid compound, said organic phases being recycled in a further oxidation, and at least one aqueous phase containing the acid produced.

18. The process according to claim 17, wherein the acid compound is extracted from the aqueous phase by crystallization.

19. The process according to, claim 9 wherein the catalyst is recycled with the organic phase(s).

20. The process according to claim 10, wherein the catalyst is separated from the liquid medium by separation by settling or solid/liquid separation.

21. The process according to claim 17, wherein the catalyst which is soluble in the aqueous phase is separated from the reaction mixture by liquid/liquid extraction, separation over resins or by electrodialysis.

22. The process according to claim 1, wherein the catalyst comprises doping elements selected from the group consisting of cobalt, copper, cerium, vanadium, chromium, bromine, zirconium, hafnium, and a combination of said elements.

23. The process according to claim 1, wherein the catalyst comprises manganese and cobalt.

24. The process according to claim 1, wherein the concentration of catalyst, expressed as manganese, in the oxidation medium is greater than 10 ppm.

25. The process according to claim 1, wherein the concentration of catalyst, expressed as manganese, in the oxidation medium is between 10 ppm and 5000 ppm.

* * * * *